United States Patent
Loos et al.

(10) Patent No.: US 12,352,763 B2
(45) Date of Patent: Jul. 8, 2025

(54) METHOD OF DETERMINING AUTOPHAGOSOME FLUX AND USES THEREOF

(71) Applicant: Stellenbosch University, Stellenbosch (ZA)

(72) Inventors: Benjamin Loos, Cape Town (ZA); Andre Du Toit, Cape Town (ZA); Jan Hendrik Servaas Hofmeyr, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 1242 days.

(21) Appl. No.: 16/099,831

(22) PCT Filed: May 10, 2017

(86) PCT No.: PCT/IB2017/052732
§ 371 (c)(1),
(2) Date: Nov. 8, 2018

(87) PCT Pub. No.: WO2017/195130
PCT Pub. Date: Nov. 16, 2017

(65) Prior Publication Data
US 2019/0113525 A1  Apr. 18, 2019

(30) Foreign Application Priority Data
May 10, 2016 (ZA) .................. 2016/03101

(51) Int. Cl.
*G01N 33/68* (2006.01)
(52) U.S. Cl.
CPC ..... *G01N 33/6893* (2013.01); *G01N 2500/00* (2013.01); *G01N 2500/02* (2013.01); *G01N 2800/24* (2013.01); *G01N 2800/2821* (2013.01); *G01N 2800/2835* (2013.01); *G01N 2800/32* (2013.01); *G01N 2800/52* (2013.01)
(58) Field of Classification Search
CPC .................. G01N 33/6893; G01N 2500/00
See application file for complete search history.

(56) References Cited

PUBLICATIONS

Loos et al. "Defining and measuring autophagosome flux—concept and reality" Autophagy (2014), 10:11, 2087-2096. (Year: 2014).*
Xiao et al. "Suppressed autophagy flux in skeletal muscle of an amyotrophic lateral sclerosis mouse model during disease progression" Physiol Rep (Jan. 2015), vol. 3, Iss. 1, e12271, 12 pages. (Year: 2015).*
Phadwal et al. (2012) "A novel method for autophagy detection in primary cells: impaired levels of macroautophagy in immunosenescent T cells" Autophagy 8:4, 677-689. (Year: 2012).*
Li et al. (Oct. 2015) "Interplay of oxidative stress and autophagy in PAMAM dendrimers-induced neuronal cell death" Theranostics, 5(12), 1363-1377. (Year: 2015).*
Loss, Benjamin, et al., "Defining and Measuring Autophagosome Flux-Concept and Reality", Autophagy, vol. 10, No. 11, pp. 2087-2096, Nov. 2, 2014, US.
Zhang, Ziao-jie, et al., "Why should autophagic flux be assessed?", Acta Pharmacologicia Sinica, vol. 34, No. 5, pp. 595-599, Mar. 11, 2013, GB.
Ganley, Ian, et al., "Distinct Autophagosomal-Lysosomal Fusion Mechanism Revealed by Thapsigargin-Induced Autophagy Arrest", Molecular Cell, vol. 42, No. 6, pp. 731-743, Jun. 24, 2011.

* cited by examiner

*Primary Examiner* — Laura Schuberg
*Assistant Examiner* — James Joseph Graber
(74) *Attorney, Agent, or Firm* — Myers Bigel, P.A.

(57) ABSTRACT

A method for measuring autophagosome flux is provided. The autophagosome pool size in a single cell is quantified, where the pool size is the total number of autophagosomes in the cell. Fusion between the autophagosomes and lysosomes in the cell is then inhibited. The autophagosome pool size is quantified over one or more time points after fusion has been inhibited, and the autophagosome flux is calculated as the initial rate of change of the autophagosome pool size at the time point after fusion has been inhibited. The method can be used to determine basal autophagosome flux, whether a cell is diseased or dysfunctional, or to diagnose a subject with a disease, disorder or dysfunction. The transition time, the time required to clear an autophagosome pool, can also be derived from the autophagosome flux. A molecule can also be characterized according to its ability to modulate autophagosome flux in a cell.

4 Claims, 11 Drawing Sheets

METHOD OF DETERMINING AUTOPHAGOSOME FLUX AND USES THEREOF

CROSS-REFERENCE TO RELATED APPLICATIONS

This application is a National Phase Application of PCT/IB2017/052732, filed May 10, 2017, which claims priority from South African provisional patent application number 2016/03101 filed on 10 May 2016, both of which are incorporated by reference herein.

FIELD OF THE INVENTION

This invention relates to a method of determining autophagosome flux in a cell, and the use thereof in the diagnosis or treatment of conditions associated with autophagy dysfunction or identifying drugs for use in treating these conditions.

BACKGROUND TO THE INVENTION

Autophagy refers to a dynamic process involved in protein and organelle degradation. Two major protein degradation systems are responsible for clearing misfolded proteins in mammalian cells. These are the proteasome and the lysosome-mediated protein degradation pathways (i.e. autophagy). Three main types of autophagy can be distinguished: macroautophagy, chaperone-mediated autophagy (CMA) and microautophagy. They differ in their cargo recognition and their fusion system with the lysosome. Macroautophagy is characterized by the delivery of regions of the cytoplasm and organelles through the formation of a double-membrane organelle (autophagosome), while microautophagy delivers cargo through a process that involves invagination of the lysosomal membrane. In contrast, CMA delivers single cytosolic proteins through a target-motif driven process, and is hence more selective (Cuervo et al., 1995). All three types result in a similar final step—lysosomal protein degradation through hydrolases.

Importantly, macroautophagy (referred to hereinafter as autophagy) is highly activated in the cellular stress response and plays an integral part of the disease pathogenesis in proteinopathies. Autophagy is a degradative pathway that is active in all eukaryotic systems in order to clear long-lived proteins. As 99% of cellular proteins are long-lived, this is clearly an important pathway. All cells are characterized by a basal level of protein degradation through autophagy under physiological conditions, in order to maintain proteostasis. This was first described in 2003 (Mizushima et al., 2003) by generating an LC3-GFP mouse model, which allowed the characterization of autophagy in all tissue types. Here it was already noted that autophagy and its magnitude and duration in upregulation in response to nutrient deprivation differs in various tissue types. Autophagy is upregulated above basal levels by a number of stimuli, such as nutrient depletion, endoplasmic reticulum stress, reactive oxygen species (ROS), hypoxia, toxic compounds, radiation and high temperature. Autophagy can thus be seen as the cell's first stress response mechanism. The mTOR kinase plays a major role in controlling the induction of autophagy, as it senses the nutrient condition and cellular energetic environment, and recruits the key protein machinery that initiates the formation of the isolation membrane.

However, the activity or rate of this process differs between cell types and tissue types. Many pathologies are associated with a change in autophagic activity. When autophagy is knocked out, mice don't survive the first few days after birth and are characterized by severe metabolic de-arrangements, suggesting lack of metabolitic substrates. The amino acid plasma levels are also depleted. This indicates the major metabolic role of autophagy under physiological conditions, to contribute towards substrate generation through protein degradation. Amino acids can be fed into the tricarboxylic acid cycle in the form of glucogenic and ketogenic amino acids, and can thereby fuel and maintain cellular respiration and ATP generation.

The primary pathologies that are associated with autophagy are neurodegeneration, cancer, heart disease and immunity. Macroautophagy is crucial for preventing neuronal protein aggregation and the onset of neurodegenerative disease, as shown in mice lacking ATG7 (Komatsu et al., 2005) and ATG5 (Hara et al., 2006). These mice develop a typical phenotype of neurodegeneration, with protein aggregation and neuronal cell death. A common feature for neurodegenerative diseases is the decline in proteostasis, with the formation of protein aggregates leading to proteo- and neuronal toxicity. Dysfunction in autophagy has been indicated in Alzheimer's disease (AD), Parkinson's disease and Huntington's disease. In fact, the dystrophic neurites described in AD are characterized by massive accumulation of autophagic vacuoles that almost completely replace the cytoplasm. It is thought that the major pathology in AD is brought about by dysfunctional fusion between autophagosomes and lysosomes, due to a dysfunctional autophagy and lysosomal machinery. Tumour cells are often characterized by a heightened basal protein degradation rate through autophagy, i.e. autophagic flux, which may transiently change in the disease pathogenesis. In addition, specific mutations (e.g. those that manifest in increased RAS-MEK signalling) are particularly characterized by increased autophagic flux and increased autophagy dependency, a phenomenon that has led to the term 'autophagy addiction'. This heightened autophagic flux and dependency often appears to manifest in a more aggressive tumour phenotype. Likewise, autophagic proficiency may increase or decrease in the course of tumour transformation, and may be of temporary or stable nature. However, the precise change of autophagic flux in the above pathologies remains largely unclear, due to the challenges to quantify the protein degradation rate through autophagy. Also, a distinction has not previously been made in the literature between autophagic flux and autophagosome flux.

One of the major focus areas in the autophagy research field is the molecular connection between autophagy and cell death susceptibility. Autophagy activity impacts the onset of cell death. This positions this pathway as a highly attractive target for therapeutic interventions, where it is desired to change the course of cellular fate. In neurodegeneration, the induction of autophagy beyond basal levels has been shown to clear toxic protein aggregates, thereby preventing neuronal cell death. Upregulation of autophagy can hence delay the induction of apoptosis onset. Due to the dynamic nature of cell death modalities, necrosis onset is also delayed. In cancer cells, the inhibition of autophagy often leads to increased apoptosis onset. However, increased autophagy also sensitizes to cancer cell death, and this paradox is thought to be flux dependent, due to the already heightened autophagic flux. Hence, one of the major unanswered questions in the field of autophagy modulation in cancer treatment deals with the relationship between the rate of protein degradation through macroautophagy, autophagy proficiency, tumour resistance and susceptibility to undergo apoptosis.

Due to the role of autophagy in impacting cellular metabolism and cell death susceptibility, major efforts are underway to better characterize autophagy inducers and inhibitors that could aid in the context of therapeutic interventions to better achieve cellular protection in the context of neurodegeneration or heart disease, and to achieve more robust cell death execution in the context of cancer chemotherapy. Major autophagy inducers include rapamycin, everolimus, CCI-779, AP23576, resveratrol, spermidine and rilmenidine, to name a few. These may operate through mTOR-dependent or independent pathways. Major autophagy inhibitors include lysosomotropic agents such as chloroquine (CQ) or hydroxychloroquine (HCQ), ATPase inhibitors such as Bafilomycin A1 or Vacuolin-1 and inhibitors such as wortmannin, 3-Methyl Adenine (3-MA) and LY294002. However, the precise extent as to which these drugs induce or inhibit autophagy remains largely unclear. Current techniques allow assessment of whether they cause a change in autophagic flux, i.e. a significant increase or decrease, but do not accurately measure the flux per se.

The present methods for assessing autophagy do not satisfactorily and accurately describe crucial information spheres, and the measurement of autophagic flux remains a major challenge in the field of autophagy. The tools currently available to assess autophagy are not particularly suitable for measuring the following autophagic fluxes as a rate:
(i) basal levels of autophagic flux under normal, physiological conditions, in all mammalian tissues and cell types;
(ii) basal levels of autophagic flux in pathology, when there is dysfunction/pathophysiology in the autophagic pathway, leading either to a pathological increase or decrease in autophagic flux;
(iii) the effect of autophagy modulators on autophagic flux, i.e. drugs that are able to upregulate or downregulate autophagic flux.

There is therefore a need for a new method of determining autophagic flux.

SUMMARY OF THE INVENTION

According to a first aspect of the invention, there is provided a method of determining autophagosome flux in a cell, the method comprising the steps of:
(i) quantifying the autophagosome pool size in a single cell over at least three time intervals, where the autophagosome pool size is the total number of autophagosomes in the cell;
(ii) inhibiting fusion between autophagosomes and lysosomes in the cell;
(iii) quantifying the autophagosome pool size over one or more time points after fusion has been inhibited; and
(iv) calculating the autophagosome flux as the initial rate of change of the autophagsosome pool size at the time point where fusion is inhibited.

When counting the number of autophagosomes in the cell, lysosomes and autophagolysosomes are excluded. These may be counted separately.

The autophagosome pool size may be quantified in step (i) when the autophagic pathway is at steady-state, i.e. when the number of autophagosomes, lysosomes and autophagolysosomes that are produced and degraded are constant.

The method may further include initial steps of transfecting the cell with an oligonucleotide encoding an LC3 protein-molecular probe conjugate, where the molecular probe is a fluorescent protein, such as a green fluorescent protein, and treating the cell with a lysosome-labelling marker, such as a dye.

The autophagosome pool size ($n_A$) may be quantified by fluorescence microscopy using z-stack image acquisition. The z-stack images may be acquired in increments of from about 0.1 to about 0.5 μm. About 5 to about 20 images per cell may be acquired for an image stack, and the images may be acquired at about 30 minute intervals over a period of from about 30 minutes to no longer than about 2 hours.

Inhibition of fusion between autophagosomes and lysosomes may be effected by treating the cell with an inhibitor. Suitable inhibitors include a lysosomotropic agent (such as chloroquine and hydroxychloroquine) or an ATPase inhibitor (such as Bafilomycin A1). The inhibitor may be added in an amount sufficient to completely inhibit the fusion of autophagosomes and lysosomes.

The method may be applied to multiple cells simultaneously.

According to a second aspect of the invention, there is provided a method of determining whether a cell in a sample is diseased or dysfunctional, the method comprising the steps of:
(i) determining the autophagosome flux of the cell according to the method described above;
(ii) comparing the autophagosome flux of the cell from the sample with a predetermined autophagosome flux of a healthy cell of the same cell type;
(iii) diagnosing the cell from the sample as diseased or dysfunctional if the autophagosome flux of this cell differs from the predetermined autophagosome flux of the healthy cell.

The disease may be Alzheimer's disease (AD), Parkinson's disease, Huntington's disease, cancer, heart disease or an immune disorder.

According to a third aspect of the invention, there is provided a method of diagnosing a disease, disorder or dysfunction in a subject, the method comprising the steps of:
(i) determining the autophagosome flux of a cell in a sample from the subject according to the method described above;
(ii) comparing the autophagosome flux of the cell from the sample with a predetermined autophagosome flux of a healthy cell of the same cell type;
(iii) diagnosing the cell from the sample as diseased or dysfunctional if the autophagosome flux of this cell differs from the predetermined autophagosome flux of the healthy cell.

The disease may be a disease which is associated with an autophagy pathology, such as diseases of neurodegeneration (e.g. Alzheimer's disease (AD), Parkinson's disease or Huntington's disease) and cancer, but may also be heart disease or an immune disorder.

According to a fourth aspect of the invention, there is provided a method of characterizing a molecule according to its ability to modulate autophagosome flux in a cell, the method comprising the steps of:
(i) quantifying the autophagosome pool size in the cell over at least three time points, where the autophagosome pool size is the total number of autophagosomes in a single cell, excluding the lysosomes and autophagolysosomes;
(ii) treating the cell with a known quantity of the molecule;

(iii) allowing the cell to reach a new steady state;
(iv) quantifying the autophagosome pool size at one or more time points once the new steady state has been reached;
(v) inhibiting fusion between autophagosomes and lysosomes in the cell;
(vi) quantifying the autophagosome pool size over one or more time intervals after fusion has been inhibited;
(vii) calculating the autophagosome flux as an initial rate of change of the autophagsosome pool size at the time point where fusion is inhibited;
(viii) comparing the autophagosome flux of the cell treated with the molecule to the autophagosome flux of a cell of the same cell type that has not been treated with the molecule to determine if there is a difference in autophagosome flux; and
(ix) characterising the molecule according to the difference in autophagosome flux.

The method may further include initial steps of transfecting the cell with an oligonucleotide encoding an LC3 protein-molecular probe conjugate, and treating the cell with a lysosome-labelling marker. The molecular probe may be a fluorescent protein, such as a green fluorescent protein, and the lysosome-labelling marker may be a dye.

The autophagosome pool size may be quantified in steps (i), (iv) and (vi) and fusion between the autophagosomes and lysosomes may be inhibited as described above.

BRIEF DESCRIPTION OF THE FIGURES

FIG. 4b shows the change in the number of autophagosomes (upper square), lysosomes (lower square), autophagolysosomes (lower circle), and total pool size (upper circle) after addition of bafilomycin A1, as shown in FIG. 4a.

FIG. 5b shows the change in the number of autophagosomes (upper square), lysosomes (lower square), autophagolysosomes (lower circle), and total pool size (upper circle) after addition of rapamycin to induce autophagosome flux, as shown in FIG. 5a.

DETAILED DESCRIPTION OF THE INVENTION

A method for measuring autophagosome flux is provided, together with applications of this method and the use of the measured autophagosome flux value.

The autophagic system is a pathway along which there is a flow of material (FIG. 1), and the quantitative measure of the rate of this flow is termed the flux through the pathway, i.e. autophagic flux. However, it is not always clear from the literature what is meant by the term autophagic flux, and a distinction between the rate at which the autophagosomal pool turns over in steady state (the autophagosome flux) and the rate at which the contents of autophagolysosomes turn over (the cargo flux), is therefore made in the description which follows.

Throughout the specification, unless the contents require otherwise, the word 'comprise' or variations such as 'comprises' or 'comprising' is intended to imply the inclusion of a stated integer or group of integers but not the exclusion of any other integer or group of integers.

The invention described herein is a process which measures autophagosomes and their rate of degradation, hence measuring autophagosome flux (i.e. not merely the number of autophagosomes). The unit of autophagosome flux is given as the rate of change in the combined autophagosome pool size (number of autophagosomes/cell/time). A feature of measuring flux according to the method of the present invention is the ability to assess separately the autophagosomal, autophagolysosomal and lysosomal pool sizes at a given time point. In this regard, a dye such as LysoTracker® (see below) can be used to distinguish between autophagosomes and autophagolysosomes (without it the green puncta would represent the sum of autophagosomes and autophagolysosomes).

The autophagosome flux in a cell is determined by:
(i) quantifying the autophagosome pool size in a single cell over at least three time intervals, where the autophagosome pool size is the total number of autophagosomes in the cell, excluding the lysosomes and autophagolysosomes;
(ii) inhibiting fusion between the autophagosomes and lysosomes in the cell;
(iii) quantifying the autophagosome pool size over one or more time points after fusion has been inhibited; and (iv) calculating the autophagosome flux as the initial rate of change of the autophagosome pool size at the time point where fusion is inhibited.

Figure 1:
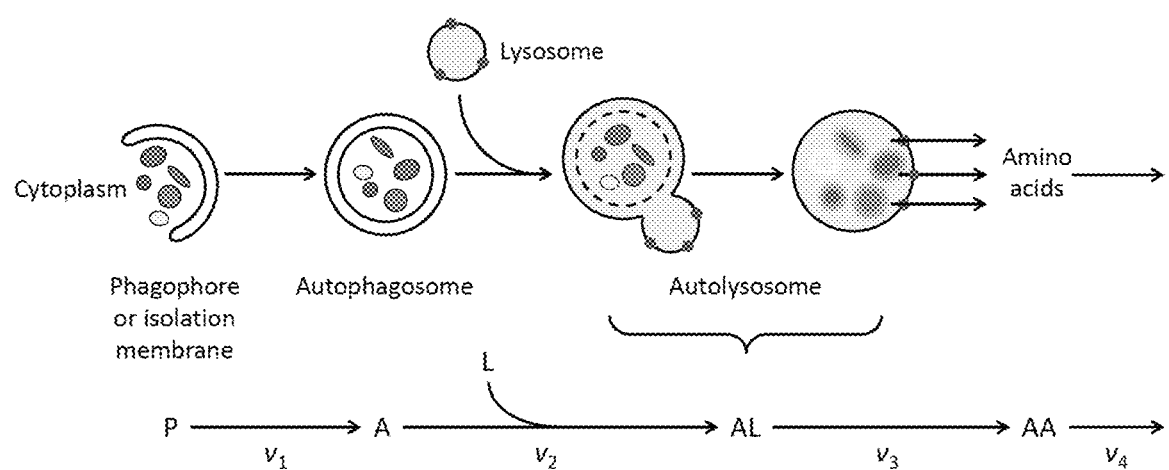
FIG. 1 is a schematic representation of the autophagy pathway viewed as a multistep pathway where each step is characterized by a rate v. The pathway depicts the entities (phagophore P, autophagosome A, lysosome L, autophagolysosome AL and amino acids AA), each of which are synthesized and degraded by a particular rate vi.

Each step in the autophagic pathway proceeds at a particular rate (v), which is quantified by the number of vesicular entities processed per time unit. The autophagic pathway is at steady state when the entities remain constant in time due to their rates of production and consumption being equal. In steady state the rates of the individual steps of the autophagic pathway shown in FIG. 1 are thus numerically equal, i.e. v1=v2=v3=v4=J. In order to measure whether the autophagic pathway is in a steady state, the pool sizes entities of the pathway need to be measured and shown to remain constant in time.

The autophagosome flux can be derived when one of the steps in the pathway is blocked. The method of the invention allows the pool sizes of the entities (i.e. the autophagosomes, lysosomes and autophagolysosomes) in a single cell to be accurately quantified, although only changes in autophagosomal pool size after fusion inhibition are used to calculate autophagosome flux.

Important features of the method include the following:
1. The ability to quantify a complete autophagosomal pool in a single cell;
2. The ability to completely block the fusion between autophagosomes and lysosomes; and
3. The ability to acquire in real time in the living cell the change of the autophagosome pool size shortly after a complete inhibition of fusion between autophagosomes and lysosomes.

The method of the present invention allows a number of novel parameters to be quantitatively described. These include the autophagosome flux J, the autophagosomal pool size $n_A$, and the autophagosomal transition time $\tau=n_A/J$, which is the time required by the cell to fill (or to clear or to turnover) its complete autophagosomal pool. The smaller $\tau$ becomes, the less time is required to completely replenish the autophagosome pool at steady state. Each parameter can now be described with its distinct unit (unlike standard techniques), where:

$n_A$=autophagosomes/cell;
J=flux (autophagosomes/hour/cell);
$\tau$=transition time (hour).

The pool size $n_A$, the flux J and the transition time $\tau$ are unique for each cell type. Additional data that can be derived from the primary data set include the cytoplasmic volume consumption rate, $J_{vol}$, and the autophagosomal membrane flux, $J_{mem}$.

The autophagosomes are measured in the complete cell volume in order to obtain the pool size (measuring the autophagosomes in a single focal plane would result in an inaccurate reading because autophagosomes that are present above and below the focal plane would be missed). Z-stack image acquisition can be performed for this purpose. An increment between the image frames in z of about 0.26-0.3 μm and an image stack of about 7-12 image frames is recommended, although a person skilled in the art would understand that other parameters might also be used. Fast image acquisition is important in order to avoid movement of autophagosomes while a single cell acquisition is being performed. For example, a wide field fluorescence system can be used, as acquisition speed is fast and phototoxicity is reduced. An excitation filter and emission for GFP is required, when using a GFP-LC3 transfection system, together with a camera such as an F-view or a confocal system with highly sensitive PMT detectors that allow rapid scanning. Temperature control and 5% $CO_2$ control is important in order to allow stable environmental conditions suitable for live cell acquisition.

For live cell acquisition, single cell acquisition in time, using automated stage coordinate settings, can be used to trace autophagosomal pool size changes from the same cell.

The surface area, $A_c$, can be used to determine the radius using equation 1, assuming the vesicle to be circular in nature:

$$r = \sqrt{\frac{4\pi}{A_c}} \tag{1}$$

The volume of the sphere, $V_s$, can be calculated using equation 2:

$$V_s = \sqrt{\frac{4}{3}\pi r^3} \tag{2}$$

Using the calculated volume data, the total surface area of spheres can be determined by multiplying the surface area of the sphere, $A_s$, which can be calculated using equation 3, with the total puncta count:

$$A_s = 4\pi r^2 \tag{3}$$

An initial count of autophagosomes over time without the use of any fusion inhibitors is required in order to determine whether the system is in a steady state. A steady state is verified over several time points when the rate of change of the number of autophagosomes/cell ($n_A$) does not change over time.

Figure 2:
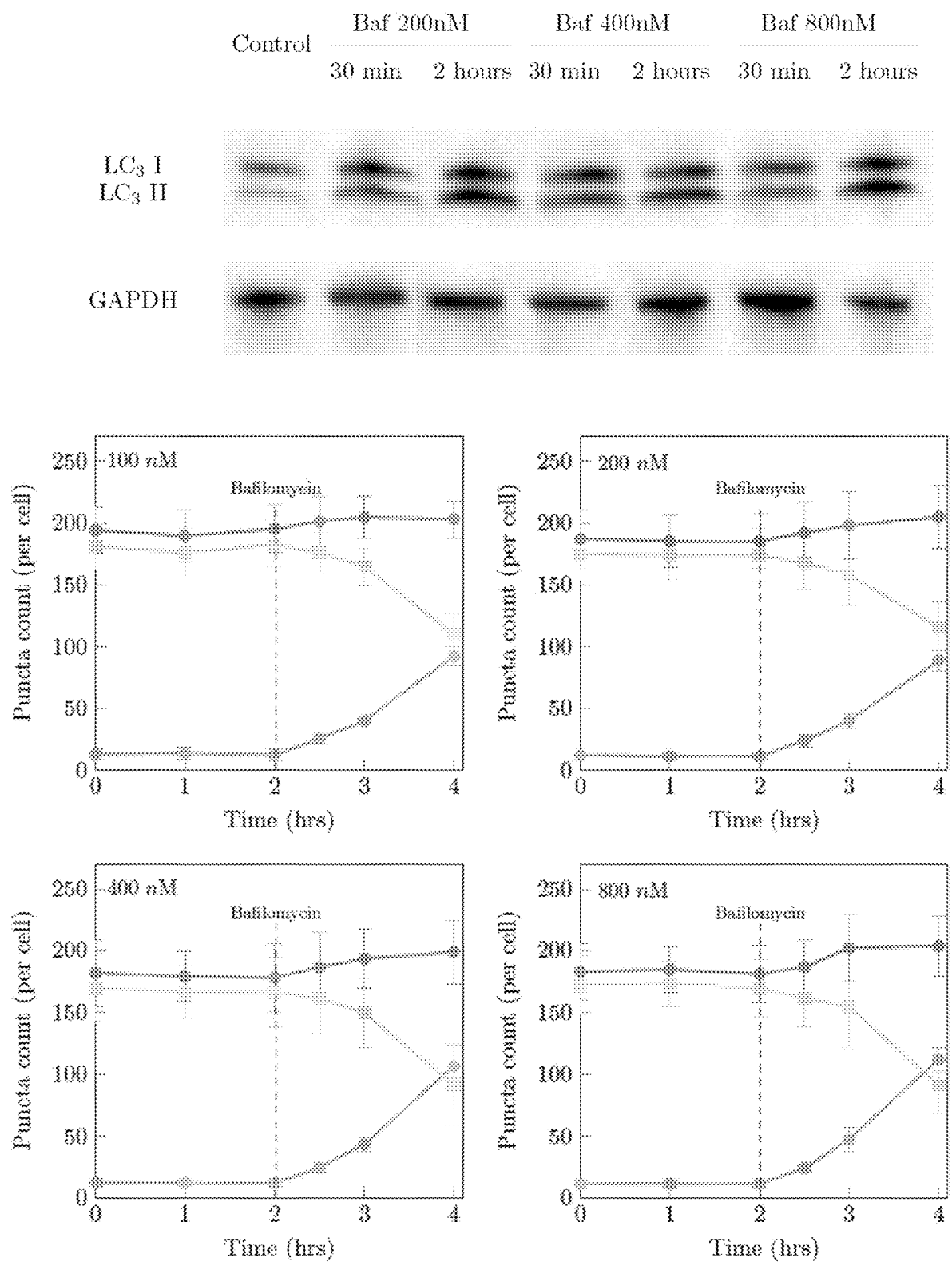
FIG. 2 is a Western blot analysis and corresponding graphs illustrating the results of the study to determine the saturating inhibitor concentration of bafilomycin A1 required to fully block autophagosomal/lysosomal fusion.

Fusion between autophagosomes and lysosomes can be temporarily blocked by treating the cell with a saturating concentration of an inhibitor, such as bafilomycin A1, leupeptin, pepstatin, or chloroquine. This saturating concentration should be determined prior to performing the method. It is characterized and achieved when an increased concentration of the inhibitor does not further increase the number of autophagosomes in the cell after treatment with the inhibitor. Although this can be performed through Western blot analysis, a more precise technique is to determine the change over time of the autophagosome pool size after inhibition of fusion using the method of the present invention (FIG. 2). Thus, the change in pool size before and shortly after inhibition of fusion is determined and the rate of change (typically expressed over 1 hour) is calculated.

If the fusion inhibitor concentration is not saturating, autophagosome flux cannot be measured accurately, since a residual flux to autophagolysosomes will remain. If the complete autophagosomal pool size cannot be quantified, autophagosome flux cannot be measured accurately. This requires a method that distinguishes between the autophagosomal pool, the lysosomal pool and the autophagolysosomal pool. If the changes in the autophagosomal pool size after inhibition of autophagosomal/lysosomal fusion cannot be measured, autophagosome flux also cannot be measured accurately. If a baseline pool size determination prior to treatment with inhibitor is not performed at at least 3 time points, no information can be gained on the nature of the steady state of the system and hence it cannot be determined whether the flux is a steady state autophagosome flux.

A short incubation time with saturating concentrations of the autophagosomal/lysosomal fusion inhibitor, such as 2 hours or less, is advisable to avoid the effects of feedback mechanisms, such as the induction of autophagosomal synthesis due to a decrease in amino acids. This would skew autophagosomal pool size analysis and would contribute to an incorrect autophagosome flux measurement.

In order to establish complete autophagosome/lysosome inhibition, a dose response with increasing inhibitor concentrations is required. This has to be performed for each cell type, as saturating concentrations as well as toxicity effects of high concentrations could be different for different cell types.

According to the method of the present invention, each cell type can be characterized by its $n_A$, J and $\tau$, and autophagosome flux at a single cell basis can be identified and calculated. Using the autophagosome flux assay of the present invention, any cell type can be characterized accordingly. This can be used to distinguish basal from deviated autophagosome flux, and diseases with autophagosome flux dysfunction can be diagnosed. Equally importantly, autophagy modulating drugs (enhancers or inhibitors) can now be accurately assessed, reporting their ability to change $n_A$, J and $\tau$. The efficacy of a drug that modulates autophagy can now be described as an index of the brought-about-change in pool size, flux and transition time: $\Delta n_A$, $\Delta J$ and $\Delta \tau$. Most conclusive will be the report of $\Delta \tau$, since it includes flux J and pool size $n_A$. The effectiveness of drugs or remedies in the treatment of a particular patient can now also be monitored.

Flux databases can also be generated. For example, each cell can be characterized with its basal autophagosome fux and/or its response to known autophagy modulating drugs, and each diseased cell or disease model system can be classified according to its autophagosome flux. Thus, comprehensive autophagic flux profiles for healthy and diseased cells can be established for use in the clinical and drug development fields.

In one embodiment of the invention, the autophagosome flux in one or more cells can be determined. For example, one or more cells are transfected with an oligonucleotide encoding an LC3 protein-molecular probe conjugate (e.g. a fluorescent protein, such as a green fluorescent protein) and treated with a lysosome-labelling marker (e.g. a dye). The autophagosome pool size in a single cell is quantified, e.g. over at least three time intervals, where the autophagosome pool size is the total number of autophagosomes in the cell. The autophagosome pool size does not include lysosomes and autophagolysosomes, which can be counted separately. This quantification of the autophagosome pool size is performed when the autophagic pathway is at steady-state, i.e. when the number of autophagosomes, lysosomes and autophagolysosomes that are produced and degraded are constant. Fusion between the autophagosomes and lysosomes in the cell is then inhibited, such as by treating the cell with an inhibitor. Suitable inhibitors include a lysosomotropic agent (e.g. chloroquine and hydroxychloroquine) or an ATPase inhibitor (e.g. Bafilomycin A1). The inhibitor should be added in an amount sufficient to completely inhibit the fusion of autophagosomes and lysosomes. The autophagosome pool size is quantified over one or more time points after fusion has been inhibited, and the autophagosome flux is calculated as the initial rate of change of the autophagsosome pool size at the time point after fusion has been inhibited.

The autophagosome pool size ($n_A$) can be quantified by fluorescence microscopy using z-stack image acquisition. The z-stack images can be acquired in increments of from about 0.1 to about 0.5 μm. About 5 to about 20 images per cell can be acquired for an image stack, and the images may be acquired at about 30 minute intervals over a period of from about 30 minutes to about 2 hours.

In another embodiment of the invention, a determination of whether a cell in a sample is diseased or dysfunctional with regard to autophagosome flux can be made. The autophagosome flux of the cell can be determined according to the method described in the above embodiment and compared to the autophagosome flux of a healthy cell of the same cell type (preferably which has been predetermined). The cell from the sample can be diagnosed as diseased or dysfunctional if the autophagosome flux of this cell differs from the predetermined autophagosome flux of the healthy cell, e.g. by a predetermined amount. Typical diseases or disorders would be those associated with a clear autophagy pathology, primarily diseases of neurodegeneration (including Alzheimer's disease (AD), Parkinson's disease and Huntington's disease) and cancer, but also include heart disease and immune disorders.

In another embodiment of the invention, a disease, disorder or dysfunction in a subject can be diagnosed. The autophagosome flux of a cell in a sample from the subject can be determined according to the method described above and compared to an autophagosome flux of a healthy cell of the same cell type. If the autophagosome flux of the cell from the subject differs from the autophagosome flux of the healthy cell, then the subject can be diagnosed with a disease, disorder or dysfunction. Typical diseases or disorders include Alzheimer's disease (AD), Parkinson's disease, Huntington's disease, cancer, heart disease or immune disorders.

In another embodiment of the invention, a molecule can be characterized according to its ability to modulate autophagosome flux in a cell. The autophagosome pool size can be quantified in a cell over at least three time points at a first steady state, where the autophagosome pool size is the total number of autophagosomes in a single cell, excluding the lysosomes and autophagolysosomes. The cell can then be treated with a known quantity of the molecule and the cell can then be allowed to reach a new (second) steady state. Once the new steady state has been reached, the autophagosome pool size can be quantified at one or more time points. Fusion between autophagosomes and lysosomes in the cell can then be inhibited (e.g. as described above). The autophagosome pool size can be quantified over one or more time intervals and the autophagosome flux can be calculated as an initial rate of change of the autophagsosome pool size at the time point where fusion is inhibited. The autophagosome flux of the cell treated with the molecule can be compared to the autophagosome flux of a cell of the same cell type that has not been treated with the molecule so as to determine if there is a difference in autophagosome flux, and the molecule can be characterized according to whether there is a difference.

The invention will now be described in more detail by way of the following non-limiting examples.

EXAMPLES

Determining Complete Fusion Inhibition

Bafilomycin A1 was selected as the inhibitor in this example because it is the most commonly used drug in the field. In FIG. 2, mouse embryonic fibroblast (MEF) cells treated at a concentration of 400 nM bafilomycin for 2 hours showed complete inhibition of autophagosomal-lysosomal fusion, although lower inhibitor concentrations may also already completely block the fusion between autophagosomes and lysosomes. At a concentration of 800 nM, cell toxicity was observed.

Sample Preparation, Acquisition and Puncta Count

For the autophagosomal pool size analysis, the autophagosomes and the lysosomes were visualized and labelled specifically. The autophagolysosomal entities were identified by co-localization analysis. Stably transfected green fluorescent protein-LC3 (GFP-LC3) cells were treated with the lysosome-labelling marker, LysoTracker® Red (Life Technologies, #L-7528) in order to visualize the autophagosomes, the lysosomes and the autophagolysosomes. MEF cells were seeded onto a sterile cover-slip patterned with large fibronectin discs (CYTOO, #10-003-10) in a CYTOO chamber single well plate. Cells were seeded at a density of $2 \times 10^4$ cells and incubated for 30 minutes. Thereafter, the chamber was rinsed several times using DMEM until all adherent cells in the non-patterned regions were washed off. The cells were maintained for 2 hours prior to the experiment in DMEM, containing 75 nM LysoTracker Red, in a humidified atmosphere in the presence of 5% $CO_2$ at 3TC. The chamber plate was then enclosed in an Olympus IX-81 stage of an inverted fluorescence microscope in the presence of 5% $CO_2$ for the duration of the experiment. Serum starvation was avoided, since it would upregulate autophagosome flux and mask the cell-inherent basal autophagosome flux.

Z-stack image acquisition was performed in order to acquire the complete autophagosomal pool size. An Olympus IX-81 coupled to an MT-20 and xenon burner 150 W and an F-view camera were employed. Temperature and 5% $CO_2$ were controlled. For live cell acquisition, single cell acquisition was performed using automated stage coordinate settings. CellR-based software (Olympus, Soft Imaging) was employed. Images were processed using Cell R imaging software and exported to the modified (for high throughput) automated counting software (ImageJ with WatershedCounting3D plug in (Gniadek et al., 2007)), to count the green and red puncta using voxel dimension 0.08 for both x and y as the search parameters. Puncta count and morphometric analysis were performed using the Watershed Counting3D plugin of ImageJ. Images were converted to RGB colour format and processed by WatershedCounting3D. Puncta count and surface area were determined for each colour puncta from the output file generated. Equations 1, 2 and 3 described above were used to determine the radius, volume and total surface area of spheres.

Determining Steady State and Basal Autophagic Flux

Figure 3A:
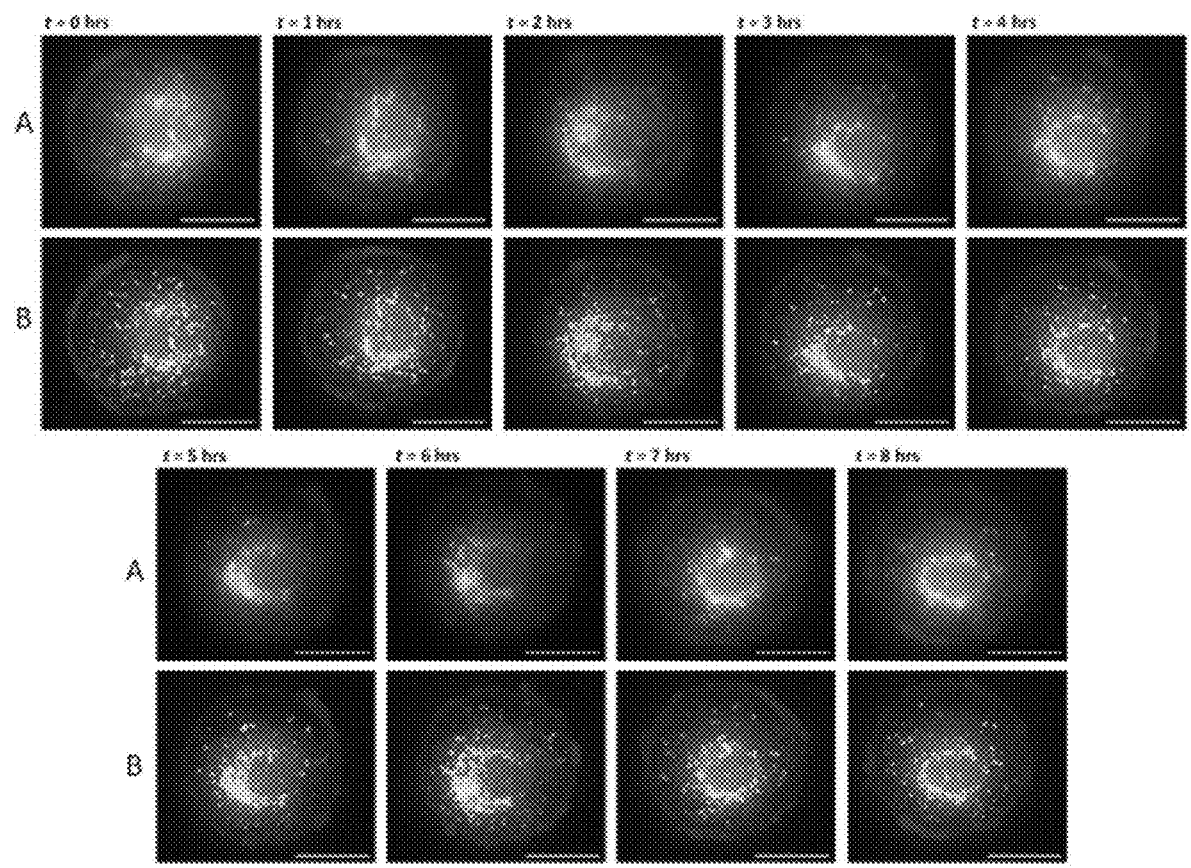
FIG. 3a shows a time lapse image sequence of autophagy in steady state under control conditions. Cells were micro-patterned and z-stack images were projected. (A) raw data; (B) deconvolved images. Scale bar: 20 μm.
Figure 3B:
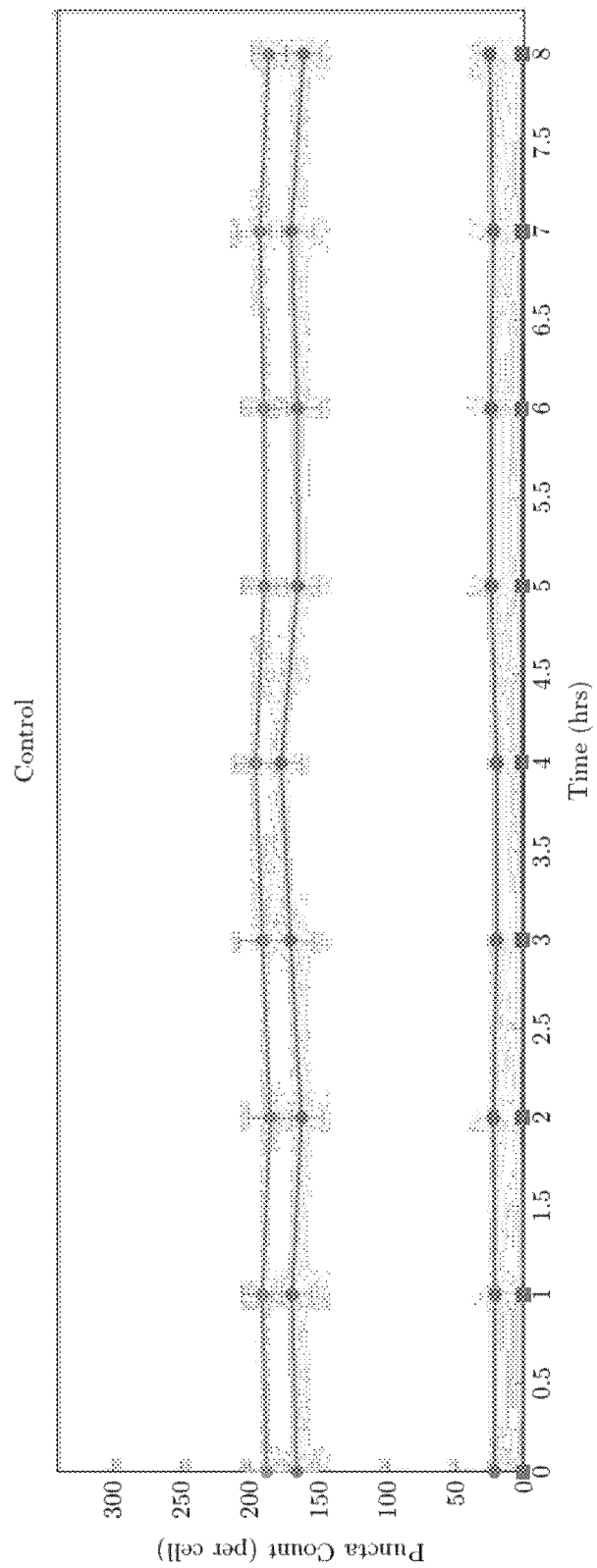
FIG. 3b is a graph showing that the pool sizes of FIG. 3a remain constant in time. Puncta are counted as autophagosomes (upper square), lysosomes (lower square) and autophagolysosomes (lower circle), with total puncta (upper circle) calculated as the sum of the three puncta types.

A steady state was verified over several time points, with cell images being acquired at time points at 0, 1, 2, 2.5, 3, 4, 5, 6.5, 6, and 8 hours (FIG. 3).

Figure 4A:
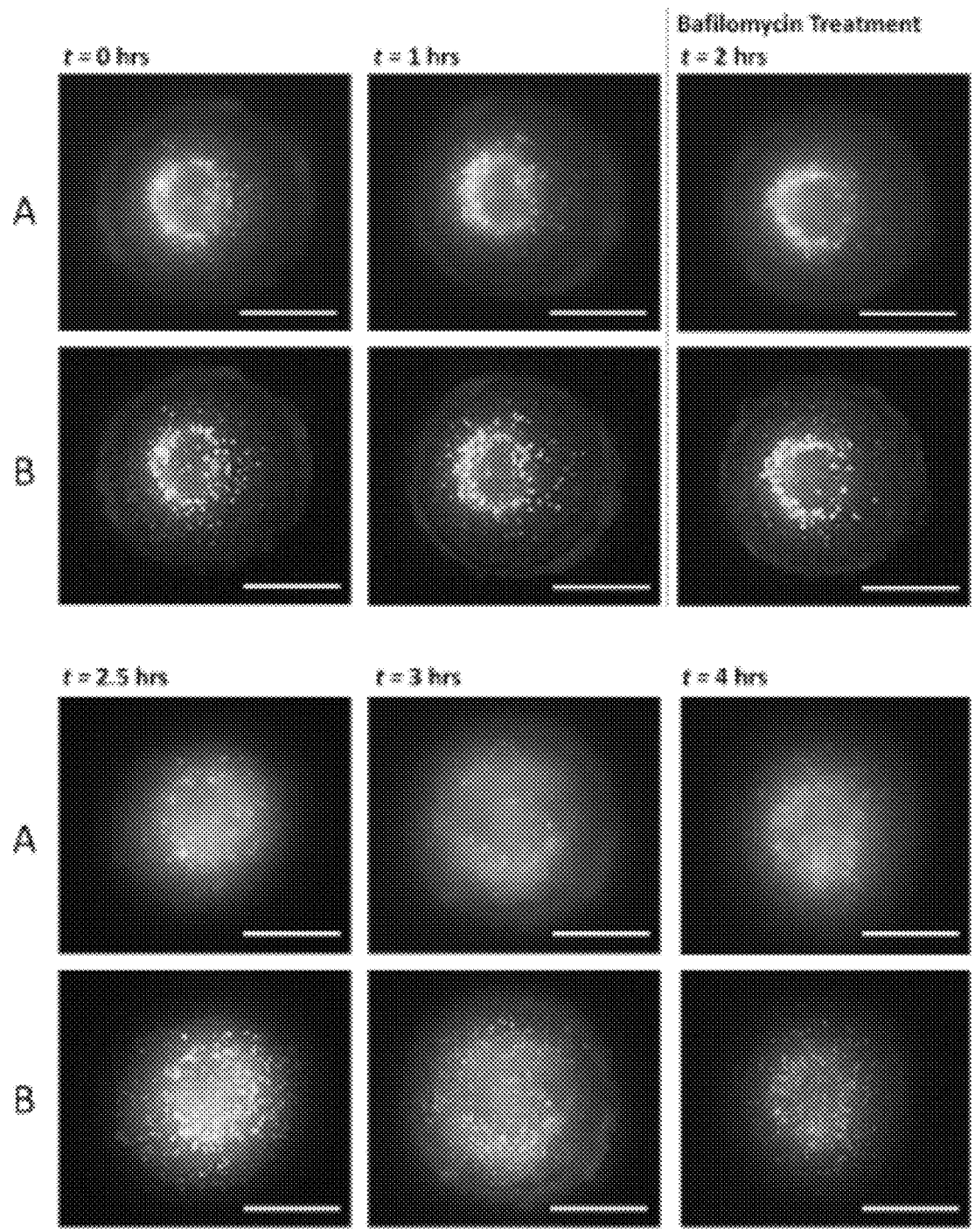
FIG. 4a shows a time lapse image sequence of basal autophagosome flux under control conditions. Cells were micro-patterned and z-stack images were projected. (A) raw data; (B) deconvolved images. Scale bar: 20 μm (n=10).
Figure 4B:
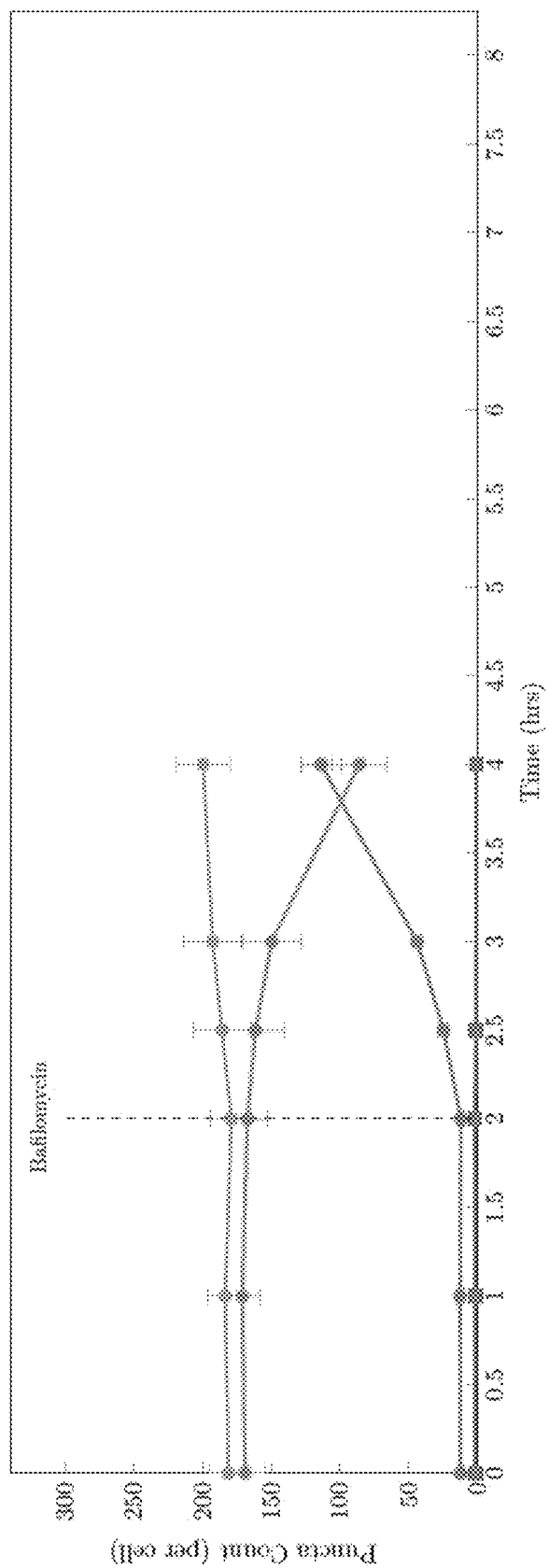

In order to assess the basal autophagosome flux in steady state, cells were treated with 400 nM bafilomycin A1 (FIG. 4). The autophagosomal pool size was monitored for two hours post-inhibition and images were acquired at 30 minute intervals. The basal flux, $J_{basal}$, was determined by allowing the autophagic system to reach a steady state under basal conditions (basal flux is the initial slope of the progress curve at the point of inhibition of fusion). Multiple cells (n=10) were assessed simultaneously using a stage control. The transition time, $\tau$, was calculated from the ratio $\tau = n_A/J$ of the autophagosome pool size and autophagosome flux, and indicated the turnover time of the autophagosome pool at steady state.

Determining Induced Autophagosome Flux

Figure 5A:
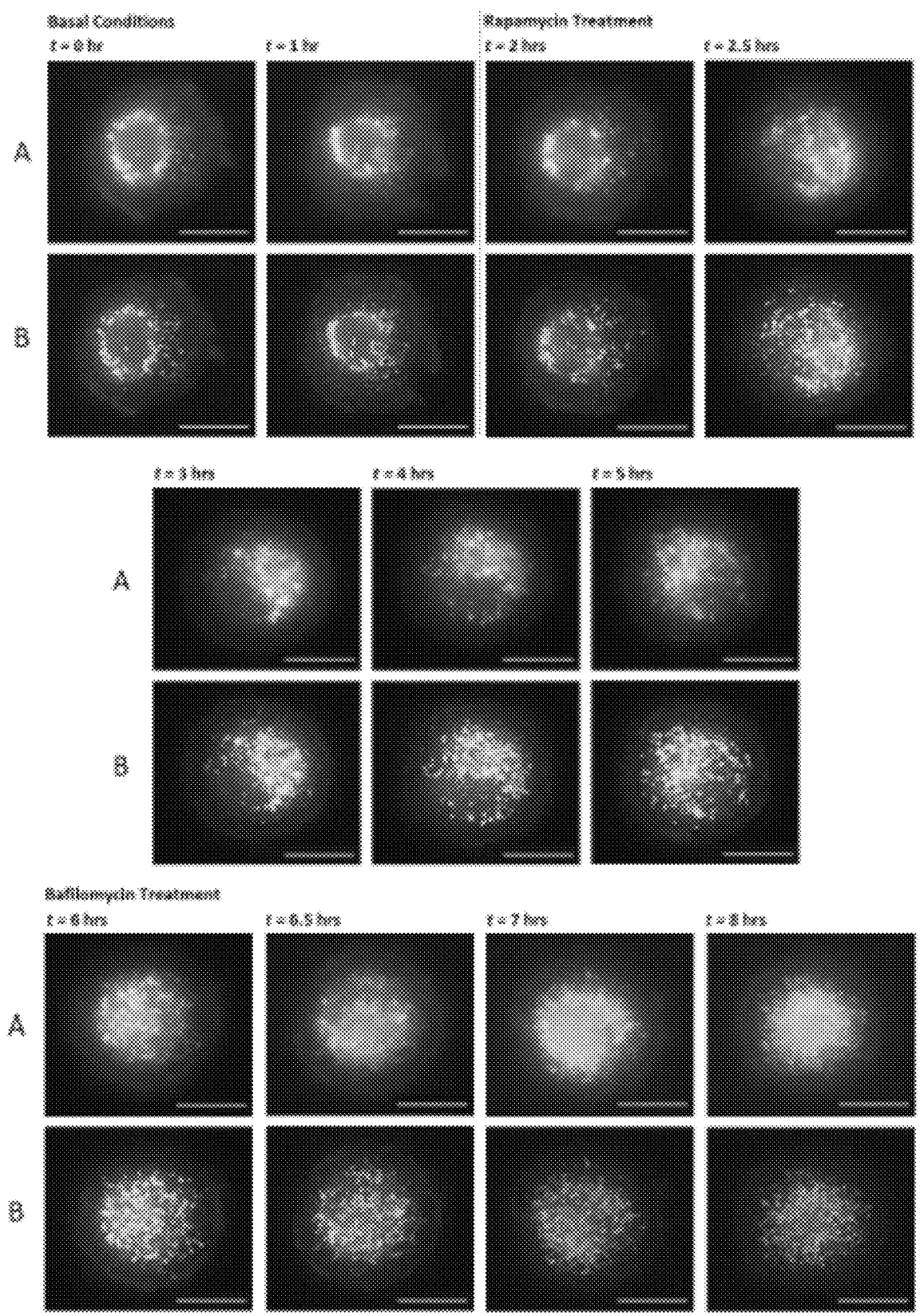
FIG. 5a shows a time lapse image sequence of induced autophagosome flux using rapamycin. Enhanced autophagy after 25 nM rapamycin treatment at 2 hr and following inhibition of fusion with 400 nM bafilomycin A1 at 6 hrs. Cells were micro-patterned and z-stack images were projected. (A) raw data; (B) deconvolved images. Scale bar: 20 μm (n=10).
Figure 5B:
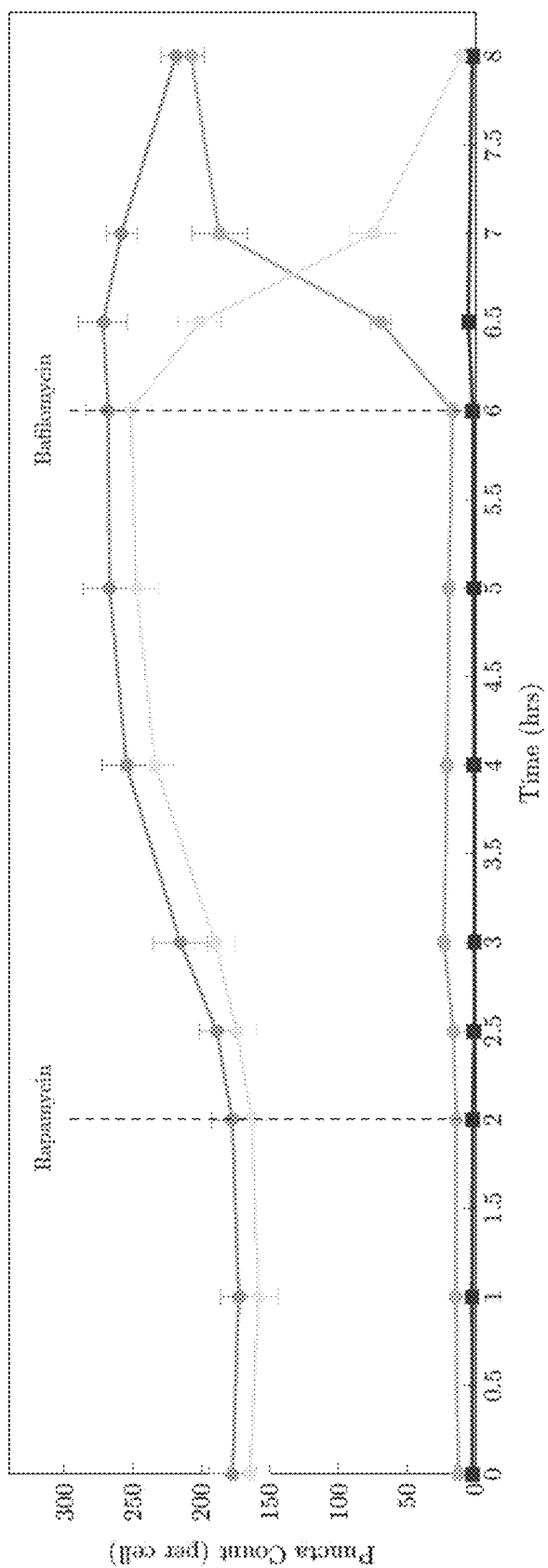

The same procedure was performed to assess the induced state, using rapamycin as an example of an autophagy inducer. Pretreatment and pool size assessment were performed prior to the use of bafilomycin in order to assess the effect of rapamycin on inducing autophagosome flux compared to basal flux (FIG. 5).

Reporting Basal and Induced Autophagosome Flux and Transition Time

Figure 6:
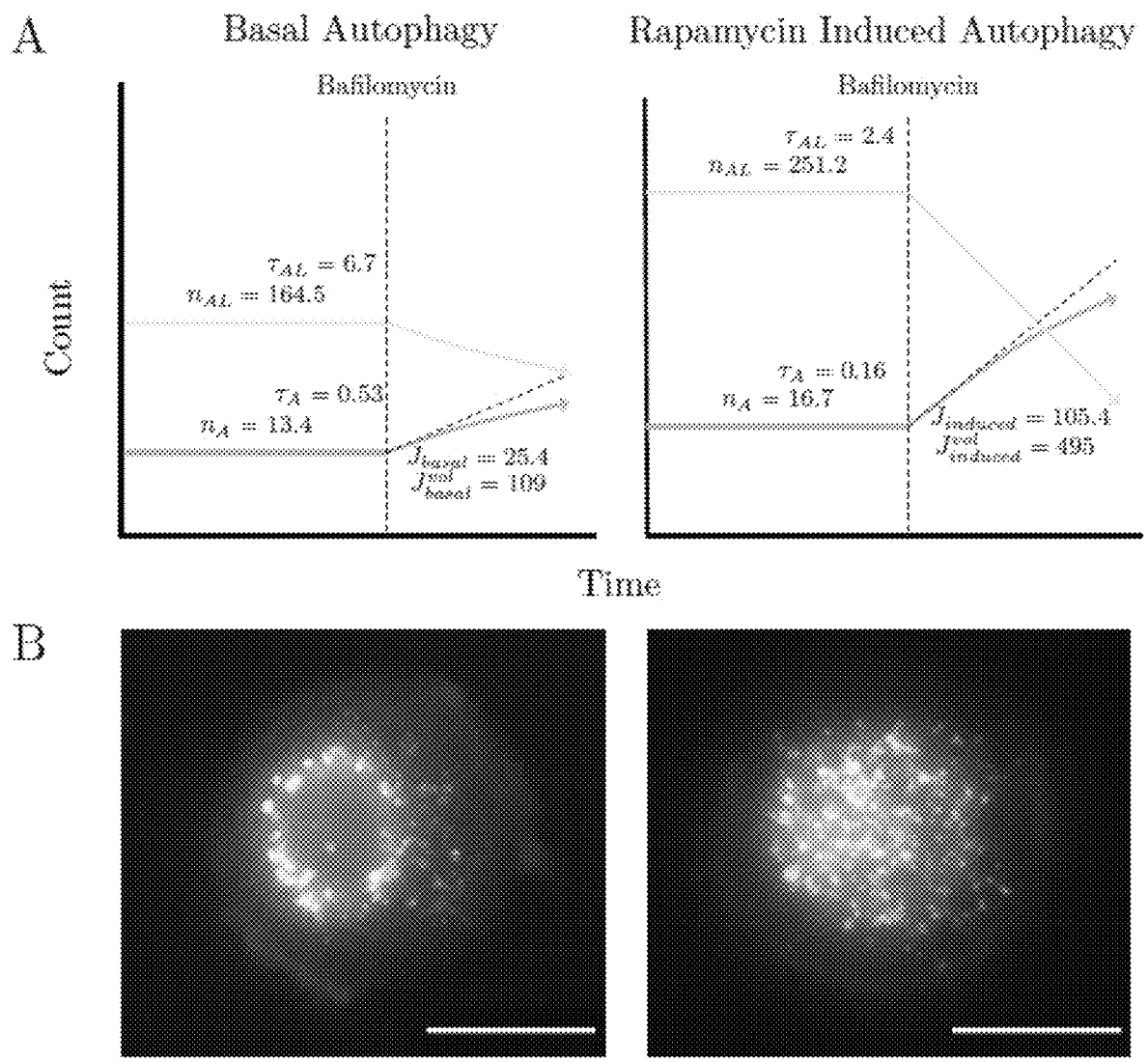
FIG. 6 is a comparison of basal flux values (A) and drug induced enhanced flux values (B). A number of novel parameters can now be quantitatively described. These include the autophagosome flux (J=autophagosomes/hr/cell), the autophagosomal pool size ($n_A$=autophagosomes/cell), and the autophagosomal transition time (τ=hr).

The autophagosome flux J, the autophagosomal pool size $n_A$, and the autophagosomal transition time $\tau$ were determined (FIG. 6 and Table 1). The transition time for the MEF cells under basal conditions was $\tau = 0.53$ hrs. When autophagy was induced, $\tau$ decreased to 0.16 hrs.

TABLE 1

MEF cells are characterized by a defined autophagosome flux (basal) which increases when using rapamycin (induced)

| Variable | Unit | Basal | Induced |
|---|---|---|---|
| Autophagosome flux, J | A/hr/cell | 25.4 | 105.4 |
| Number of autophagosomes, $n_A$ | A/cell | 13.4 | 16.7 |
| Number of autophagolysosomes, $n_{AL}$ | AL/cell | 164.5 | 251.2 |
| Average volume of an autophagosome | fL | 4.3 | 4.7 |
| Average volume of an autophagolysosome | fL | 17.3 | 18.8 |
| Autophagosomal transition time, $\tau_A$ | hr | 0.53 | 0.16 |
| Autophagolysosomal transition time, $\tau_{AL}$ | hr | 6.7 | 2.4 |
| Cytoplasmic volume consumption rate, $J_{vol}$ | fL/hr/cell | 109 | 495 |
| Autophagosomal membrane flux, $J_{mem}$ | $\mu m^2$/hr/cell | 1397 | 8268 |

Upregulation of autophagy by using 25 nM rapamycin increased autophagosomal pool size by 22.4%, autophagosome flux by 315% and led to a decrease in transition time by 69.8% (Table 2).

TABLE 2

MEF cells are characterized by a defined autophagosome flux (basal) which increases when using rapamycin (induced). This increase can be precisely expressed as the net change ($\Delta$) or as % change (% $\Delta$), comparing autophagosome pool size, autophagosome flux and transition time

| MEF cells | Basal | Modulator (Rapamycin) | $\Delta$ | % $\Delta$ |
|---|---|---|---|---|
| Autophagosome Pool size nA No. of autophagosomes | 13.4 | 16.4 | 3 | 22.4 |
| Autophagosome flux J No. of autophagosomes/cell*hr[1] | 25.4 | 105.4 | 80 | 315 |
| Transition time hr | 0.53 | 0.16 | 0.37 | 69.8 |

Validation Against Standard Techniques

The autophagosome flux tool was validated against Western blot analysis and transmission electron microscopy (TEM), two currently available standard techniques that assess autophagy but which have not previously been used to measure autophagosome flux. Western blot analysis and TEM was performed in the presence and absence of bafilomycin A1.

Figure 7:
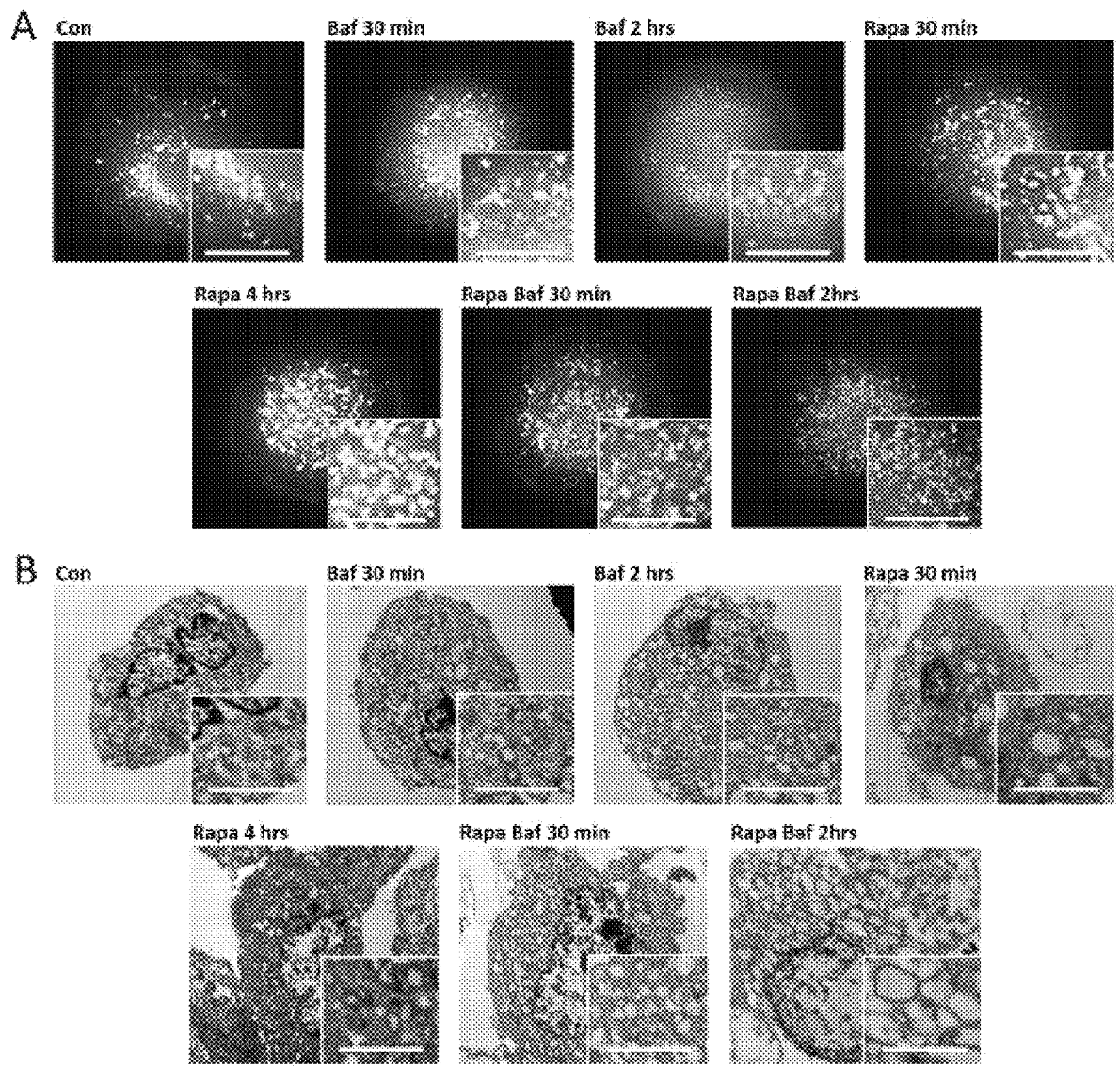
FIG. 7 is a representation of the validation results. TEM-based analysis provides good ultrastructural detail, but omits to acquire data in real time of a complete cell (z-stack) that report on the entities autophagosomes, autophagolysosomes and lysosomes.

The autophagosome flux assay tool was shown to be much more accurate than the other two techniques. This is because it allows the description of $n_A$, J and $\tau$. Moreover, it derives the micrograph-based data from z-stack data sets, thereby including all focal planes that belong to the sample of interest. This provides a complete and accurate count of the autophagy intermediates. In contrast, TEM-based analysis provided, even when morphometrics was being performed, only data derived from a single focal plane, rendering any morphometric analysis incomplete (FIG. 7). Moreover, the nature of TEM, which requires fixation, does not allow the tracking of the same cell in real time, omitting the measurements of dynamic changes in morphometric counts. TEM analysis also allows the identification of generic vacuolar structures only (FIG. 7), without a clear distinction between autophagosomes, lysosomes and autophagolysosomes.

Figure 8:
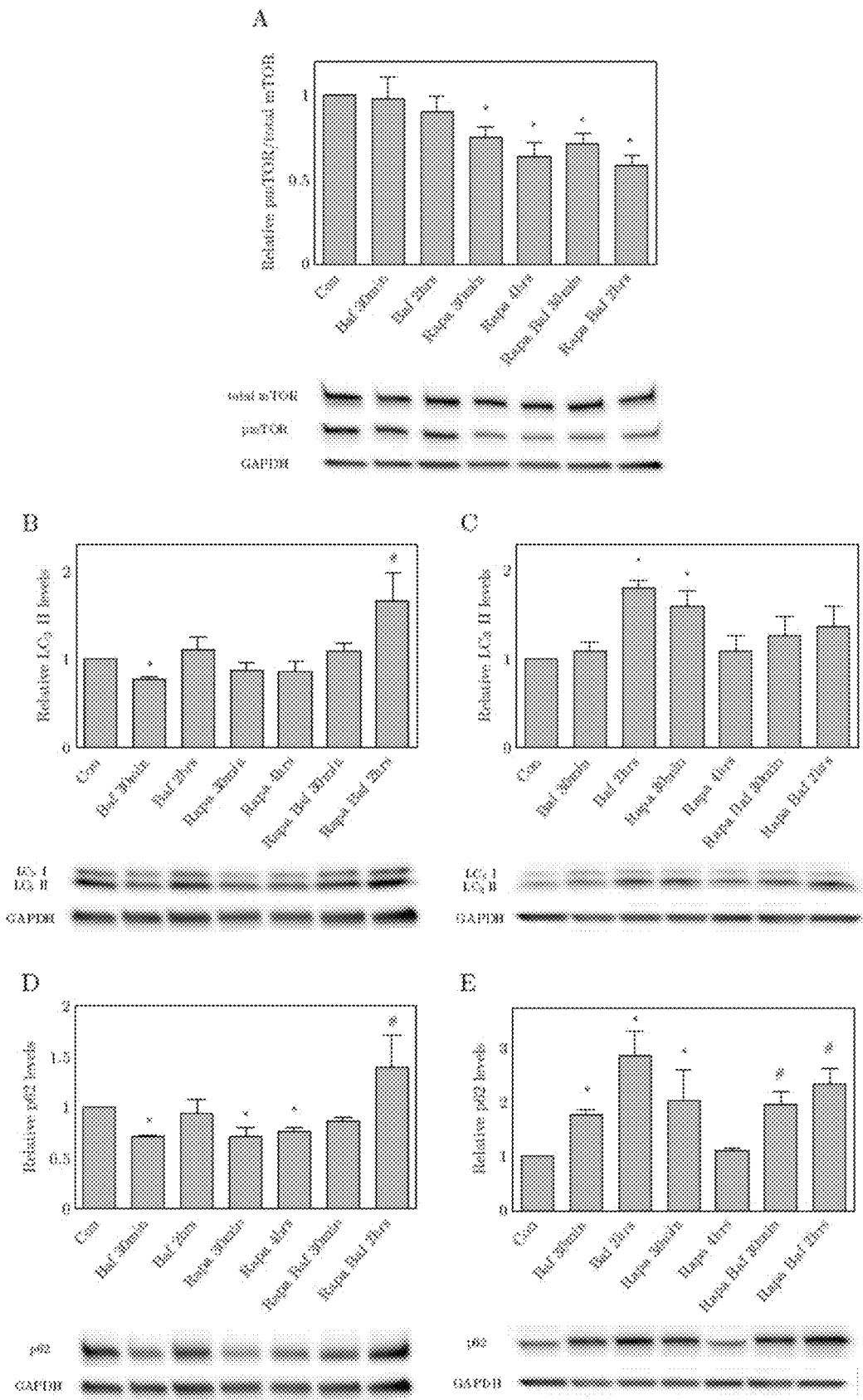
FIG. 8 is a Western blot analysis probing for LC3, p62 and pmTOR. The figure reveals merely that the flux status is changing, i.e. increasing or decreasing, since treatment with bafilomycin increases LC3II and p62 bands. This method, however, cannot measure dynamic changes and vesicular pool size required to measure autophagosome flux.

The Western blot analysis at similar time points clearly suggests that it is not suitable for measuring pool size data of single cells in time. Therefore, autophagosome flux cannot be accurately assessed. It allows the detection of the respective protein, LC3 II, from a whole cell population, without linking the protein band signal to single cell pool sizes of entities. Moreover, the nature of Western blot analysis omits any measurements of dynamic changes (FIG. 8). Western blot analysis reports only on the flux status, i.e. whether flux is significantly increased or decreased.

TEM and Western blot analysis are therefore useful techniques to use as a guiding method to report an indication for the flux status of cells, but the actual and distinct flux value can be determined according to the method described herein.

REFERENCES

Cuervo, A. M., Knecht, E., Terlecky, S. R., Dice, J. F., 1995. Activation of a selective pathway of lysosomal proteolysis in rat liver by prolonged starvation. Am. J. Physiol. 269, C1200-1208.

Mizushima, N. et al., 2004. In vivo analysis of autophagy in response to nutrient starvation using transgenic mice expressing a fluorescent autophagosome marker. Molecular biology of the cell, 15(3), pp. 1101-11.

Komatsu, M., Waguri, S., Ueno, T., Iwata, J., Murata, S., Tanida, I., Ezaki, J., Mizushima, N., Ohsumi, Y., Uchiyama, Y., Kominami, E., Tanaka, K., Chiba, T., 2005. Impairment of starvation-induced and constitutive autophagy in Atg7-deficient mice. J. Cell Biol. 169, 425-434.

Hara, T., Nakamura, K., Matsui, M., Yamamoto, A., Nakahara, Y., Suzuki-Migishima, R., Yokoyama, M., Mishima, K., Saito, I., Okano, H., Mizushima, N., 2006. Suppression of basal autophagy in neural cells causes neurodegenerative disease in mice. Nature 441, 885-889.

Loos, B., Toit, A. du & Hofmeyr, J.-H. S., 2014. Defining and measuring autophagosome flux—concept and reality. Autophagy, 10(11), pp. 2087-2096.

Gniadek, T. J. and Warren, G, 2007. WatershedCounting3D: A new method for segmenting and counting punctate structures from confocal image data. Traffic 8, 339-346.

The invention claimed is:

1. A method of identifying a molecule as having the ability to modulate autophagosome flux in a cell, the method comprising the steps of:

(i) transfecting a cell with a DNA molecule encoding a microtubule-associated protein 1 light chain 3 (LC3) protein-molecular probe conjugate so as to identify all of the autophagosomes and autophagolysosomes in the cell;

(ii) treating the cell with a lysosome-labelling marker so as to distinguish the autophagolysosomes from the autophagosomes;

(iii) quantifying the autophagosome pool size in a single cell over at least three time intervals to determine when the autophagic pathway is at steady-state, where the autophagosome pool size is the total number of autophagosomes in the cell that are not co-localized with the lysosome-labelling marker, the autophagosome pool size therefore excluding the autophagolysosomes;

(iv) treating the cell with a known quantity of the molecule;

(v) quantifying the autophagosome pool size at one or more time points once a new steady state has been reached, where the autophagosome pool size is the total number of autophagosomes in the cell that are not co-localized with the lysosome-labelling marker, the autophagosome pool size therefore excluding the autophagolysosomes;

(vi) inhibiting fusion between the autophagosomes and lysosomes in the cell when the autophagic pathway is at steady-state by treating the cell with a fusion inhibitor;

(vii) quantifying the autophagosome pool size over one or more time points after fusion has been inhibited, where the autophagosome pool size is the total number of autophagosomes in the cell that are not co-localized with the lysosome-labelling marker, the autophagosome pool size therefore excluding the autophagolysosomes;

(viii) calculating the autophagosome flux as an initial rate of change of the autophagosome pool size at the time point where fusion is inhibited, wherein the autophagosome flux is independent of the change in the number of autophagolysosomes after fusion has been inhibited; and (ix) identifying the molecule as upregulating autophagic flux when the autophagic flux of the cell is increased relative to the same cell type that has not been treated with the molecule or identifying the molecule as down regulating autophagic flux when the autophagic flux of the cell is decreased relative to the same cell type that has not been treated with the molecule.

2. The method according to claim 1, wherein the inhibitor is a lysosomotropic agent or an ATPase inhibitor.

3. The method according to claim 2, wherein the lysosomotropic agent is chloroquine, hydroxychloroquine or Bafilomycin A1.

4. The method according to claim 1, wherein the molecular probe conjugate is a fluorescent protein.

* * * * *